(12) United States Patent
Dean et al.

(10) Patent No.: US 7,682,696 B2
(45) Date of Patent: Mar. 23, 2010

(54) MEDICAL ARTICLE AND METHOD OF MAKING AND USING THE SAME

(75) Inventors: Jennifer Dean, Eindhoven (NL); David B. Engel, The Woodlands, TX (US); David Gascoyne, Schenectady, NY (US); Jessica Hanley Budris, Troy, NY (US); Daniel R. Olson, Voorheesville, NY (US); Radislav Potyrailo, Niskayuna, NY (US); Philippe Schottland, Evansville, IN (US); Marc Wisnudel, Clifton Park, NY (US)

(73) Assignee: Sabic Innovative Plastics IP B.V. (NL)

( * ) Notice: Subject to any disclaimer, the term of this patent is extended or adjusted under 35 U.S.C. 154(b) by 1533 days.

(21) Appl. No.: 10/985,135

(22) Filed: Nov. 10, 2004

(65) Prior Publication Data

US 2006/0054526 A1 Mar. 16, 2006

Related U.S. Application Data

(63) Continuation-in-part of application No. 10/939,632, filed on Sep. 13, 2004, now abandoned.

(51) Int. Cl.
*B32B 27/18* (2006.01)
*B32B 27/20* (2006.01)
*B32B 27/30* (2006.01)
*B32B 27/36* (2006.01)

(52) U.S. Cl. ............... 428/412; 428/522; 428/913; 422/55; 422/58; 422/119; 116/206; 215/201; 215/203; 215/230

(58) Field of Classification Search ............... None
See application file for complete search history.

(56) References Cited

U.S. PATENT DOCUMENTS

| 2,606,654 | A | | 8/1952 | Davis et al. | |
|---|---|---|---|---|---|
| 3,406,069 | A | * | 10/1968 | Overman | 430/507 |
| 3,480,402 | A | * | 11/1969 | David | 422/56 |
| 3,635,895 | A | | 1/1972 | Kramer | |
| 3,896,965 | A | | 7/1975 | Cornell | |
| 3,935,960 | A | | 2/1976 | Cornell | |
| 4,001,184 | A | | 1/1977 | Scott | |
| 4,012,554 | A | * | 3/1977 | Miller et al. | 503/213 |
| 4,094,642 | A | | 6/1978 | Sumimoto et al. | |
| 4,121,714 | A | * | 10/1978 | Daly et al. | 206/363 |
| 4,169,811 | A | * | 10/1979 | Yoshikawa et al. | 436/138 |
| 4,194,622 | A | * | 3/1980 | Lewis | 206/363 |
| 4,206,844 | A | * | 6/1980 | Thukamoto et al. | 206/439 |
| 4,217,438 | A | | 8/1980 | Brunelle et al. | |
| 4,238,524 | A | | 12/1980 | LaLiberte et al. | |
| 4,298,569 | A | * | 11/1981 | Read | 422/27 |
| 4,407,960 | A | * | 10/1983 | Tratnyek | 436/1 |
| 4,480,760 | A | * | 11/1984 | Schonberger | 215/230 |
| 4,489,841 | A | | 12/1984 | Thompson | |
| 4,495,291 | A | * | 1/1985 | Lawton | 436/1 |
| 4,505,399 | A | * | 3/1985 | Weiner | 215/230 |
| 4,519,515 | A | * | 5/1985 | Schonberger | 215/230 |
| 4,526,752 | A | * | 7/1985 | Perlman et al. | 422/56 |
| 4,687,113 | A | | 8/1987 | Reeve | |
| 4,755,405 | A | | 7/1988 | Massucco et al. | |
| 4,759,713 | A | | 7/1988 | Heiss et al. | |
| 4,816,305 | A | | 3/1989 | Stillwell et al. | |
| 4,859,360 | A | * | 8/1989 | Suzuki et al. | 252/299.7 |
| 4,886,338 | A | * | 12/1989 | Yafuso et al. | 385/12 |
| 4,890,763 | A | * | 1/1990 | Curiel | 229/102 |
| 4,905,851 | A | | 3/1990 | Thompson | |
| 4,961,954 | A | * | 10/1990 | Goldberg et al. | 600/36 |
| 4,980,222 | A | | 12/1990 | Rivera et al. | |
| 4,986,429 | A | | 1/1991 | Singleton, Jr. | |
| 5,005,873 | A | | 4/1991 | West | |
| 5,064,576 | A | * | 11/1991 | Suto | 556/37 |
| 5,104,704 | A | | 4/1992 | Labes et al. | |
| 5,142,018 | A | | 8/1992 | Sakashita et al. | |
| 5,151,491 | A | | 9/1992 | Sakashita et al. | |
| 5,152,412 | A | | 10/1992 | Her | |
| 5,201,921 | A | | 4/1993 | Luttermann et al. | |
| 5,206,118 | A | * | 4/1993 | Sidney et al. | 430/343 |
| 5,228,573 | A | | 7/1993 | Pavelle et al. | |
| 5,234,732 | A | * | 8/1993 | Versic et al. | 428/35.7 |
| 5,314,072 | A | | 5/1994 | Frankel et al. | |
| 5,329,127 | A | | 7/1994 | Becker et al. | |
| 5,344,017 | A | | 9/1994 | Wittrock | |
| 5,452,379 | A | | 9/1995 | Poor | |
| 5,477,972 | A | | 12/1995 | Lester | |
| 5,501,945 | A | * | 3/1996 | Kanakkanatt | 430/338 |

(Continued)

FOREIGN PATENT DOCUMENTS

EP 0 116 892 B1 12/1988

(Continued)

OTHER PUBLICATIONS

U.S. Appl. No. 10/889,913; filed Jul. 13, 2004; Authenticatable Article and Method of Authenticating.

(Continued)

*Primary Examiner*—Vivian Chen
(74) *Attorney, Agent, or Firm*—Cantor Colburn LLP

(57) ABSTRACT

The packaged medical article can comprise the medical article and a protective layer capable of inhibiting exposure of the medical article to a color change activator prior to use of the medical article. The medical article comprises a plastic portion and an active color changing specie, wherein the color changing specie is capable of changing color after exposure to a color change activator. The method for producing a medical article can comprise: combining thermoplastic resin with a blocked color changing specie to form a resin mixture and manufacture processing the resin mixture to form a packaged medical article. This manufacturing processing comprises forming the resin mixture into the medical article and packaging the medical article to form a packaged medical article. The color changing specie will not affect the structural integrity of the medical article when it changes color.

18 Claims, No Drawings

U.S. PATENT DOCUMENTS

| | | | |
|---|---|---|---|
| 5,510,619 A | | 4/1996 | Zachmann et al. |
| 5,553,714 A | | 9/1996 | Cushman et al. |
| 5,573,909 A | | 11/1996 | Singer et al. |
| 5,582,887 A | | 12/1996 | Etheredge |
| 5,623,812 A | * | 4/1997 | Todt ............................ 53/442 |
| 5,703,229 A | | 12/1997 | Krutak et al. |
| 5,786,132 A | | 7/1998 | Nohr et al. |
| 5,881,196 A | | 3/1999 | Phillips |
| 5,885,672 A | | 3/1999 | Phillips et al. |
| 5,955,025 A | * | 9/1999 | Barrett ......................... 422/28 |
| 5,990,199 A | | 11/1999 | Bealing et al. |
| 6,033,762 A | | 3/2000 | Decker |
| 6,063,551 A | | 5/2000 | Nohr et al. |
| 6,096,387 A | | 8/2000 | Decker |
| 6,099,930 A | | 8/2000 | Cyr et al. |
| 6,200,628 B1 | | 3/2001 | Rozumek et al. |
| 6,238,623 B1 | * | 5/2001 | Amhof et al. ................. 422/58 |
| 6,254,969 B1 | | 7/2001 | Eberle |
| 6,267,242 B1 | | 7/2001 | Nagata et al. |
| 6,296,911 B1 | * | 10/2001 | Catarineu Guillen ......... 428/29 |
| 6,297,508 B1 | | 10/2001 | Barmore et al. |
| 6,317,947 B1 | | 11/2001 | Ruschmann |
| 6,375,069 B1 | | 4/2002 | Smith |
| 6,402,986 B1 | | 6/2002 | Jones, II et al. |
| 6,436,616 B1 | * | 8/2002 | Geisler et al. ................ 430/350 |
| 6,460,726 B1 | | 10/2002 | Hierzer et al. |
| 6,500,526 B1 | | 12/2002 | Hannington |
| 6,503,559 B1 | | 1/2003 | Nohr et al. |
| 6,514,617 B1 | | 2/2003 | Hubbard et al. |
| 6,607,744 B1 | * | 8/2003 | Ribi ............................ 424/439 |
| 7,026,029 B2 | | 4/2006 | Lindholm et al. .......... 428/64.1 |
| 7,244,252 B2 | | 7/2007 | Berndt ........................... 606/1 |
| 7,459,259 B2 | * | 12/2008 | Engel et al. .............. 430/270.1 |
| 2002/0000392 A1 | | 1/2002 | Searle |
| 2002/0012610 A1 | * | 1/2002 | Dufresne et al. .............. 422/28 |
| 2002/0197478 A1 | * | 12/2002 | Muggli et al. ............ 428/411.1 |
| 2003/0127846 A1 | | 7/2003 | Laurie |
| 2003/0211618 A1 | * | 11/2003 | Patel ............................ 436/38 |
| 2004/0043254 A1 | | 3/2004 | Wisnudel et al. |
| 2004/0050740 A1 | * | 3/2004 | Lewis ...................... 206/459.1 |
| 2004/0175522 A1 | * | 9/2004 | Tajima ...................... 428/35.7 |
| 2007/0017042 A1 | * | 1/2007 | Cincotta et al. ................ 8/643 |

FOREIGN PATENT DOCUMENTS

| | | |
|---|---|---|
| EP | 0368456 A1 | 5/1990 |
| EP | 0 404 402 B1 | 8/1993 |
| EP | 0 467 619 B1 | 10/1994 |
| EP | 0 544 699 B1 | 10/1994 |
| EP | 0 625 467 A1 | 11/1994 |
| EP | 0 548 283 B1 | 9/1995 |
| EP | 0672509 A2 | 9/1995 |
| EP | 0 627 363 B1 | 4/1996 |
| EP | 1356830 A2 | 10/2003 |
| FR | 2521906 A1 | 8/1983 |
| GB | 2 264 558 A | 9/1993 |
| GB | 2 330 408 A | 4/1999 |
| WO | WO 84/03270 | 8/1984 |
| WO | WO 90/03632 | 4/1990 |
| WO | WO 92/03502 | 3/1992 |
| WO | WO 92/12068 | 7/1992 |
| WO | WO 95/13229 | 5/1995 |
| WO | WO 96/12659 | 5/1996 |
| WO | WO 98/37819 | 9/1998 |
| WO | WO 99/588619 | 11/1999 |
| WO | WO 01/40792 A1 | 6/2001 |
| WO | WO 01/86289 A1 | 11/2001 |
| WO | WO 01/98426 A1 | 12/2001 |
| WO | WO 02/00206 A2 | 1/2002 |

OTHER PUBLICATIONS

U.S. Appl. No. 10/867,309; filed Jun. 14, 2004; Tagged Resin, Method of Making a Tagged Resin, and Articles Made Therefrom.
JP6286769; Publication Date Oct. 11, 1994; Tamper-Evident Seal; Abstract; only one page.
JP10281894; Publication Date Oct. 23, 1998; Display Material; Abstract; only one page.
International Search Report, International Application No. PCT/US2005/032163; International Filing Date: Aug. 9, 2005; Applicant's file reference: 08CL157601; 7 pages.
US 4,448,317, 05/1984, Thompson (withdrawn)

* cited by examiner

MEDICAL ARTICLE AND METHOD OF MAKING AND USING THE SAME

CROSS REFERENCE TO RELATED APPLICATIONS

This application is a continuation-in-part of U.S. application Ser. No. 10/939,632 filed on Sep. 13, 2004, now abandoned which is herein incorporated by reference.

BACKGROUND

A major problem confronting the various makers and users of products made from thermoplastic resins such as telecommunication products, consumer electronic products, automotive parts, medical devices or containers, and identification documents (e.g., identity (ID) cards, credit cards, etc.), has been the unauthorized reproduction or copying of such products or articles by unauthorized manufacturers, sellers, and/or users. Such unauthorized reproduction is often referred to as piracy and can occur in a variety of ways, including consumer level piracy at the point of end use as well as wholesale duplication at the commercial level. Regardless of the manner, piracy deprives legitimate manufacturers of significant revenue and profit. In addition, in many cases, piracy is associated with manufacturer liability. In fact, piracy could tarnish the image of a brand by associating defective counterfeit products with reputable companies.

In the case of the pharmaceutical industry, the consequences of piracy and counterfeiting may be even more severe than in other industries because the health of the patients may be at stake. The growing concerns around that industry attracted the attention of the Federal Drug Administration (FDA) who released a report on February 2004 containing recommendations to fight drug counterfeiting. Similarly, single use devices (SUDs) are also being looked at by the FDA because of the growing number of reprocessed SUDs that are inappropriately being used. Defective or contaminated devices might have catastrophic consequences on the outcome of a surgery. Although actual guidelines or standards for implementing security solutions have not been established at this time, this industry is looking for solutions to authenticate and track original products at various points in the supply chain. For drug containers and medical devices, it is also desirable to have the ability to confirm if an article has been tampered with or used.

Automated identification of plastic compositions is desirable for a variety of applications, such as recycling, tracking the manufacturing source, antipiracy protection, and others. A variety of identification methods of plastic materials are known, including X-ray and infrared spectroscopy and the use of tags in plastic materials, e.g., UV and near-IR fluorescent dyes added to polymers for identification purposes. Fluorescence lifetime of an embedded dye can also be used for the identification purposes. In addition to the use of organic fluorophores, inorganic tracers were used such as yttrium vanadate, zinc sulfide (ZnS) associated to one metal, and organometallic materials.

Tamper evident labels, tapes, wrappers, and seals have been disclosed as a solution to protect drug containers or packages against tampering. Another common way of protecting pharmaceutical containers is the use of special closure systems that cannot be resealed after opening without leaving obvious evidence of tampering for example by including frangible parts in the closure system. Example of other technologies to protect against tampering, re-use, or re-sterilization also include tamper resistant package with an outer shattering layer.

In the case of medical devices such as those used in surgical procedures, a common way of protecting against re-use is to use indicators or labels that are sensitive to sterilization techniques. Another way of protecting devices against use after re-sterilization is to engineer the device so that the conditions of the sterilization will affect the mechanical properties or shape of an essential component rendering the whole device unusable.

There remains a need for articles and methods for determining authenticity and/or for determining if tampering has occurred.

SUMMARY

Disclosed herein are medical articles and methods of making and using the same. In one embodiment, the packaged medical article can comprise the medical article and a protective layer capable of inhibiting exposure of the medical article to the color change activator prior to use of the medical article. The medical article comprises a plastic portion and an active color changing specie, wherein the color changing specie is capable of changing color after exposure to a color change activator.

In another embodiment, the medical article can comprise a plastic portion and a blocked color changing specie. The color changing specie is capable of being active after post-processing; wherein the post-processing is different than manufacturing processes employed to make the medical article. The active color changing specie is capable of changing color after exposure to a color change activator. The color change and the post-processing do not affect the structural integrity of the medical article.

In one embodiment, the method for producing a medical article can comprise: combining thermoplastic resin with a blocked color changing specie to form a resin mixture and manufacture processing the resin mixture to form a packaged medical article. This manufacturing processing comprises forming the resin mixture into the medical article and packaging the medical article to form a packaged medical article. The color changing specie will not affect the structural integrity of the medical article when it changes color.

The above described and other features are exemplified by the following detailed description.

DETAILED DESCRIPTION

It is noted that the terms "first," "second," and the like, herein do not denote any amount, order, or importance, but rather are used to distinguish one element from another, and the terms "a" and "an" herein do not denote a limitation of quantity, but rather denote the presence of at least one of the referenced item. Additionally, all ranges disclosed herein are inclusive and combinable (e.g., the ranges of "up to 25 wt %, with 5 wt % to 20 wt % desired," are inclusive of the endpoints and all intermediate values of the ranges of "5 wt % to 25 wt %," etc.). The modifier "about" used in connection with a quantity is inclusive of the stated value and has the meaning dictated by the context (e.g., includes the degree of error associated with measurement of the particular quantity). The notation "±10%" means that the indicated measurement may be from an amount that is minus 10% to an amount that is plus 10% of the stated value. Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. It is also noted that "medical" as used herein, includes dental, pharmaceutical, and the like.

This disclosure presents methods of tagging containers and articles that can be used to provide security solutions, e.g., to help the pharmaceutical industry fight counterfeiting, and to detect tampering and/or use (such as for drug containers and medical devices). In one embodiment, the container comprises a modified thermoplastic resin with built-in sensitivity to a color change activator (e.g., light, oxygen, and/or the like). In the case of resin used for medical devices, the resin could have a built-in sensitivity to color change activators such as light, oxygen, chemicals from rinsing/cleaning solutions (e.g. acid, base sensitivity), sterilization chemicals (e.g., hydrogen peroxide, ethylene oxide, and the like), body fluids (e.g., blood, plasma, and the like), special sterilization processes (such as gamma radiation sterilization, electron beam sterilization, and the like), and the like, as well as combinations comprising at least one of the foregoing sensitivities. Upon exposure to a color change activator (e.g., removing from the packaging, tampering, using, reprocessing, and so forth), the active leuco dye, for example, easily converts to its oxidized form (for instance by an oxidation process involving the presence of oxygen), thereby absorbing light at a higher wavelength than the leuco form. This absorption is generally located in the visible part of the electromagnetic spectrum thus leading to the formation of a visible color.

In containers or medical devices, the built-in sensitivity could be visually detectable (for example an appearance or visible color change in the container/device), or may use a detector (e.g., an excitation source). In one embodiment, the containers can be produced directly in a sensitive form immediately after injection-molding or extrusion (e.g., the article is oxygen sensitive immediately after molding and significant exposure to oxygen/air would result in a visible color change). For example, a significant color change from an original color would correspond to a CIELAB $\Delta E^*$ value of greater than or equal to about 5 units, or, more specifically, greater than or equal to about 10 units, and more specifically, greater than or equal to about 20 units. The affect of exposure of the color changing specie to the color change activator can be controlled to attain a color change in a desired period of time. For example, a CIELAB $\Delta E^*$ of greater than or equal to 5 units, or, more specifically, greater than or equal to about 10 units, in a desired period. If an essentially immediate color change is desired, a change can occur in less than a few minutes. If a slow color change is desired, a change can occur after several hours. For example, for a surgical instrument, a significant color change could occur after a desired period of greater than or equal to about 8 hours, or, more specifically, greater than or equal to about 12 hours, or, even more specifically, greater than or equal to about 24 hours, after initial exposure to the color change activator, wherein, in less than the desired period, the CIELAB $\Delta E^*$ is less than or equal to 4 units, or, more specifically, less than or equal to 3 units. Unless otherwise specified, CIELAB $\Delta E^*$ value is determined using a sphere instrument (10 nanometer (nm) resolution color spectrophotometer; e.g., Gretag MacBeth 7000A) and the instrument settings are: UV included, SCI, D65 illuminant and 10 degree observer). Additionally, unless otherwise specified, transparent and slightly translucent samples (ASTM D1003 percent haze (% haze) $\leq$10) will be measured in transmission mode, whereas heavily translucent samples (% haze $\geq$10) and opaque samples will be measured in reflectance mode with white tile backing. Spectrophotometric data are collected in accordance with ASTM methods E1164 and CIELAB values are calculated by the spectrophotometer software in accordance with ASTM E308.)

In another embodiment, the containers can be produced in a non-activated form (blocked) that can later be activated by a secondary operation (e.g., a post-processing) such as exposure to light (e.g., UV photoflash), heat (e.g., heat pulse), cleaning and/or sterilization processes (e.g., autoclaving, gamma radiation sterilization, ethylene oxide sterilization, electron beam radiation sterilization, enzymatic cleaning, disinfecting solution, and the like), and the like, as well as combinations comprising at least one of the foregoing secondary operation (wherein the light, heat, sterilizers, cleaners, etc., are "deblockers"). For example, container/device/article (hereinafter medical article) can be handled similar to those formed from standard thermoplastic resin until they are activated with the secondary operation. UV exposure can be used during adhesive curing operations used to bond parts during medical device assembly (e.g., a stopcock valve on a trocar). During the curing operation, the trocar is exposed to UV light that can cause deblocking (e.g., activation) of the color changing specie. In other words, a blocked color changing specie can be used initially blocked for facile processing and manufacturing. During (or after) the manufacturing process (e.g., before or after packaging), the blocked color changing specie can be activated such that it will change color after exposure to the color change activator. If deblocking is intended to occur after the manufacturing process, the deblocking mechanism for the blocked color changing specie should be different than processing employed during manufacturing.

The chemistry of the color changing specie can be selected such that the color changing process is initially delayed to allow for handling and packaging operations to proceed. An example of this process would be the use of a color changing specie having hydrolysable blocking group, the use of groups that are photosensitive to ambient light, and the like, as well as combinations comprising at least one of the foregoing. Some possible blocking groups include a carbamate, thiocarbamate, enamine, imine, acetal, sulfenyl, sulfonyl, phosphoryl, alkyl, imide, amide, benzylic moiety, peptide moiety, protein moiety, and the like, as well as combinations comprising at least one of the foregoing blocking groups. In yet a further embodiment, the color change can be from a low chroma color (e.g., white, gray, and so forth) to a higher chroma color (e.g., blue, green, and so forth). Optionally, the color change specie can be chemically bound (e.g., covalently bonded) to the resin.

For example, a medical article having the built-in sensitivity (either as a whole or in some component(s) of the article) can be medical devices used in surgical operations, such as a trocar, a harmonic scalpel, a stapler, and the like. The color change can be initiated upon opening a sealed package containing the article. Alternatively, the article can have a built-in usage/exposure indicator. For example, the article can be a trocar having a housing and/or obturator (or cap) that connects onto the housing, wherein the housing is molded from the resin with the color changing specie.

The color change can be a general color change of the entire surface of the article, or the color change can provide a specific pattern or text message. For example, the color change can result in elimination of the name of the original manufacturer and/or other text. To achieve such a result, the color change must result in a decrease in contrast between the printed information on the article and the remainder of the article. A color change may indicate that an article: (i) has been removed from its original package, (ii) has been used, (iii) has been tampered with, (iv) has been reprocessed, (v) is no longer covered by the manufacturer warranty, and so forth, as well as combinations comprising at least one of the foregoing. For example, the article is a stapler or a harmonic scalpel. The color changing specie can be a component of the material used to make all or a portion of the article (e.g., the handle, the housing, and/or the trigger of the article) such that a color change occurs after the device is removed from its original package, used, or reprocessed. Note that the portion of the article that contains the color changing specie can be opaque or transparent. The selection of an opaque or transparent matrix will be based on functional requirements (e.g. transparency needed to see through the part, or opaque glass filled material needed to have a high modulus, add strength and/or reduce the thermal expansion coefficient of the material), as well as aesthetic requirements for the device.

The built-in sensitivity can be a color/appearance change (hereinafter color change), wherein the color/appearance change can be such that: (i) a lightness of the container or device (CIELAB L*) will drop by greater than or equal to about 10 units when measured in transmission or reflectance mode using a D65 source and a 2-degree illuminant; (ii) a total light transmission through the container wall, measured according to ASTM D1003, decreases by greater than or equal to about 10%; (iii) (for transparent containers and devices) the lightness or light transmission changes can be such that the visibility through the container reduces so as to affect functionality (for instance: one cannot clearly see: what is inside the container, a liquid/filling level, printings on the container, device features are no longer visible, and/or the like); and the like, as well as combinations comprising at least one of the foregoing changes. For example, the equipment can originally be clear (e.g., almost colorless), have a light color (e.g., amber), or the like, after molding. After use (e.g., tampering or otherwise exposure to the color change activator, the color (in an area or of the entire equipment) can switch to a dark (e.g., almost black) color.

For example, the resin used to produce the equipment can change color as a result of a marking process induced by light (e.g., Xenon lamp exposure, UV lamp exposure, UV or visible diode laser exposure, and the like, as well as combinations comprising at least one of the foregoing). This color change can be throughout the equipment, or in an area (e.g., spots, text, alphanumerical characters; e.g., an inscription such as "do not reuse" or "device used by XYZ", "used", "contaminated" "obsolete", "opened", a date, and the like, as well as combinations comprising at least one of the foregoing). The marking (e.g., color change) can be automatic or can be initiated; e.g., by a medical professional (e.g., surgeon, physician, nurse, and the like). For example, the medical professional can "mark" the item by triggering an irreversible local or total color change of the container or device by exposing it to a particular light source. This marking can be used to "obsolete" the part (e.g., for instance turning a clear part into a dark part). During a future medical procedure, a medical professional will inspect devices/containers and readily know if it has been previously made "obsolete" (by checking if the device/container has undergone a color change) and validate the use based on the result of the inspection.

Examples of color changing species includes organic color matter (e.g., organic molecules) that undergo a color change following an oxidation process. In one embodiment, the color changing species will be added to a resin during the formation of the article. Optionally, the color changing species can be materials having enough heat stability to be processed with the plastic material such that the plastic pellets used to form the medical article will have built-in color changing capability. The color changing specie can be present in a separate layer (e.g., film) that is applied to the device (e.g., by an IMD (in-mold decoration) process). In such case, the additive can be dispersed in the film material, and/or applied by a coating process, screen printing process, or the like, on top of the film. Such process may be useful when the color changing specie has a heat or processing stability that is not sufficient to be compatible with the extrusion/injection molding process used to produce the device. The color changing species can be in a non-ionic form, e.g., that can be transformed into an ionic form of a different color, e.g., upon exposure to a color change activator. The color changing specie can be in a form that is not oxygen sensitive. In a further embodiment, the color changing specie can be in a non-ionic form that is a blocked reduced form of a colorant. Essentially, the color changing specie can be in a stable form while being handled. The stable state can be a permanent state (e.g., no specific shelf life for the additive) or could be limited to a certain period of time (e.g. core-shell encapsulated activated additives). Organic color changing species can be in a leuco form that has been made stable by blocking and/or encapsulation thus allowing the color changing specie to be handled in the presence of the color change activator during the manufacturing process. The blocking group can maintain the molecule in a blocked leuco form (i.e., in a state where the electronic conjugation in the chromophore is interrupted). After an activation/deblocking step, the leuco form becomes sensitive to the color change activator (the electronic conjugation is no longer interrupted) resulting in a visible color change after exposure to the color change activator.

Color changing species can include dyes, dyestuff, charge-transfer complexes, absorbers, colorants, pigments, complexes, and the like, hereinafter collectively "coloring matter", wherein dyes can be advantageous since they disperse into a resin matrix without adding haze to the material, and therefore the dye can be used for both transparent and opaque applications. Possible color changing species include leuco coloring matter, such as the leuco form of the azine coloring matter family (e.g., thiazine, oxazine, phenazine, phenoxazines, phenothiazines and the like), leuco aryl methane coloring matter, leuco indigo coloring matter, and the like, as well as derivatives and combinations comprising at least one of the foregoing color changing species, with dyes of these color changing species advantageous. Some examples of such coloring matter include the leuco form of methylene blue and basic blue 3. Formula I represents a generic structure for the leuco form of a blocked azine dye (i.e., an inactive material) (X=N for phenazine; X=O for phenoxazines, and X=S for phenothiazines). Formula I sets forth a generic structure of a blocked azine leuco dye:

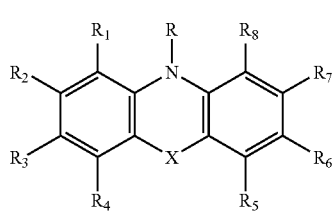

Formula I

In Formula I, X in Formula I can be O or S. $R_1$ to $R_8$, individually, represent a halogen atom, a hydroxy group, an amino group, an alkyl group, an alkylamino group, a dialkylamino group, an alkyl ether group, a cycloalkyl group, a cyclic ether group, an aryl group, an aryl ether group, a heterocyclic group, a sulfonyl group, a carbonyl group, an ester group, a carbonate group, or the like. Adjacent substituents may also be part of a fused ring. R can be, for example, a substituent that forms a urethane, amide or a thioamide bond with the leuco dye, and can have sufficient heat stability to sustain the manufacturing process (e.g., an extrusion and molding process). Non-limiting examples of substituents include acyl groups ester groups and thioester groups (e.g., —CO-M, where M represents an organic substituent such as an alkyl, aryl, an alkoxy, an aryloxy, or a sulfonyl substituent), and so forth. In one embodiment, R is a benzoyl group. Formula II represents benzoyl leuco methylene blue (BLMB) a blocked leuco dye that is gamma radiation sensitive (i.e., deblocked) during gamma irradiation.

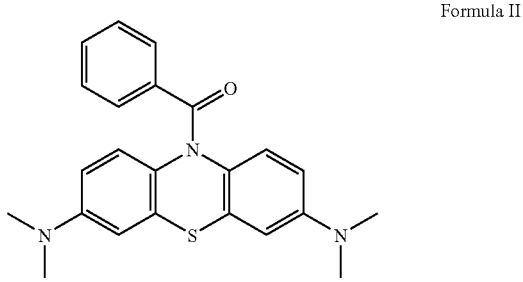

Formula II

In another embodiment, the R group on the leuco dye can be a peptide moiety or a peptide substructure such as —CO—CHR$_9$—NR$_{10}$R$_{11}$, wherein R$_9$, R$_{10}$, and R$_{11}$ can be a hydrogen atom, an organic substituent (linear or cyclic) that can, optionally, contain a heteroatom (e.g., Cl, Br, F, N, S, P, O, and so forth, as well as combinations comprising at least one of the foregoing) and can, optionally, be unsaturated; and so forth, as well as combinations comprising at least one of the foregoing. It is noted that peptide moieties typically contain proteases that cleave peptide or protein moieties into amino acids or their derivatives, and can, therefore, be the blocking group to detect the exposure to enzymatic cleaning solutions.

Other exemplary color changing species comprise the blocked form of an aryl methane derivative (e.g., aryl methane, aryl carbinol, and the like, as well as combinations comprising at least one of the foregoing), such as leuco aryl methanes (e.g., leuco Crystal Violet, leuco Malachite Green, and the like). Formula III sets forth structures of these types of dyes.

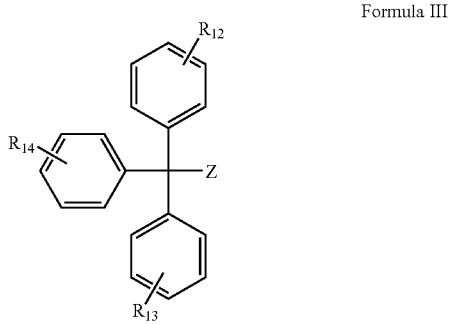

Formula III

In a blocked aryl methane dye, Z can be O-acyl, O-aryl, O-alkyl, N-acyl, N-aryl, N-alkyl, O-silyl, S-alkyl, S-aryl, Si-alkyl, Si-aryl, Si-alkoxy, sulfonyl (—O—SO$_2$—R$_{15}$, where R$_{15}$ is a linear or cyclic organic substituent such as alkyl, aryl, a perfluorinated organic group, or the like), a photolabile carbonyl group (—CO-D wherein D is an aryl group; such as those described in U.S. Pat. No. 5,786,132). In another embodiment, Z can be an amide group (—CO—R$_{16}$), such as a benzoyl group, which can be primarily cleaved during gamma radiation sterilization. Z can be a carbonate group (—O—CO—O-E) where E can be an aryl substituent. Z can be a carbamate group (N—CO—O—R$_{16}$), wherein R$_{16}$ can be an organic substituent. Note that R$_{12}$-R$_{14}$ can, individually, be single or multiple substituents (optionally cyclic or fused rings) that can be tailored to modify the electronic conjugation in the dye and form a broad range of colors when the aryl methane dye is in its oxidized form. Possible substituents include, for example, hydrogen, alkyl-amino groups, aryl-amino groups, halogens, alkoxy groups, aryloxy groups, acyl groups, aryl groups, alkyl groups, and the like, as well as combinations comprising at least one of the foregoing. Z can also be a combination comprising at least one of any of the foregoing Zs.

Other color changing species such as heterocyclic aza- or thio-aromatic dyes can be used in their active leuco form, such as the dyes of Formulas IV and V:

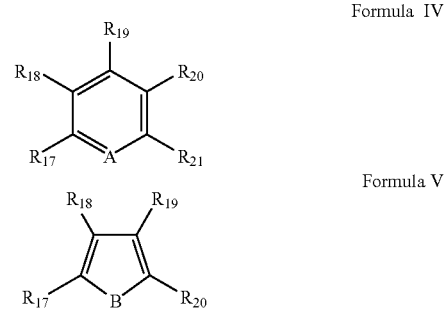

Formula IV

Formula V

A can be C—R$_{22}$, NH, O, S+, or N—R$_{21}$; and B can be C—R$_{22}$, NH, O, S, or N—R$_{22}$; while R$_{17}$-R$_{22}$ can be H, alkyl, aryl, acyl, halogen, thiocarbamate, enamine, imine, acetal, sulfenyl, sulfonyl, phosphoryl, or imide.

In the blocked form, the dyes of Formulas IV and V can be protected (e.g., blocked), in a variety of manners. For example, if A and/or B is NH, the blocking group would replace the H (i.e., N—R$_{23}$), wherein the blocking group (R$_{23}$) could be a variety of blocking groups as described above. Exemplary blocking groups include, —CO-phenyl, —SO$_2$—C$_6$H$_5$, —CO—C—(CH$_3$)$_3$, —CO$_2$C$_2$H$_5$, —CO-phenyl-NH$_2$, —CO-phenyl-alkyl, —CO-phenyl-alkoxy, —CO-phenyl-halogen, —SO$_2$C$_4$H$_9$, -tosyl, and the like, as well as combinations comprising at least one of any of the above blocking groups. Other possible protecting groups are set forth in *Protective Groups in: Organic Synthesis*, by Theodora W. Greene and Peter G. M. Wuts, Third Edition, John Wiley & Sons, Inc., New York, N.Y. (1999); and in *Chemistry and Applications of Leuco Dyes*, edited by Muthyala, by Tran Van Thien, Plenum Press, New York, N.Y. (1997).

In one embodiment, a blocked color changing specie (e.g., blocked leuco dye) can be encapsulated in a resin (e.g., in a resin comprising an oxygen permeability of less than or equal to about 1.1 Barrers, wherein Barrer is defined in Equation I), $$1 \text{ Barrer} = 10^{-10} \frac{\text{cm}^3 (STP)\text{cm}}{\text{cm}^2 s \cdot \text{cmHg}} \qquad \text{Equation I}$$

such as acrylic resins (e.g., PMMA), and so forth. Encapsulation can be carried out, for example, by emulsion polymerization in the presence of the blocked color changing specie, or by direct emulsion polymerization (e.g., where the blocking group on the color changing specie comprises an acrylate moiety and/or a vinyl moiety).

The size of the particles formed by emulsion polymerization can be controlled to create a desired particle size. For example, core-shell particles may be formed, i.e. a core containing the color changing specie dispersed in a first matrix and an outer shell containing a second matrix, which could be the same as the first matrix, that will create an oxygen barrier layer by lowering the oxygen diffusion rate. The size of the particle and/or shell as well as the degree of crosslinking and the nature of the encapsulation material can be tailored to provide the desired oxygen sensitivity as well as the desired appearance. For transparent applications, to avoid/limit light scattering, a particle size of less than or equal to about 100 nanometers (nm) can be employed, or, more specifically, a particle size of less than or equal to about 50 nm. Alternatively, or in addition, to tailoring the particle size, an encapsulation matrix can be selected with a refractive index (RI) close to the RI of the resin to which the color changing specie will be added. A refractive index difference of less than or equal to about 0.005 can be employed from an optical properties standpoint. Other properties, such as heat stability and especially oxygen permeability, are also parameters considered in the selection of the encapsulation matrix. Unless set forth to the contrary, all particle sizes are median particle size ($d_{50}$) as measured along the major axis, e.g., using transmission electron microscopy (TEM).

Optionally, color changing species can be disposed in the plastic resin, in a coating, an adhesive, or otherwise between resin layers, inside the medical article (e.g., inside a clear container), on the outside of the container, and the like, as well as combinations comprising at least one of the foregoing. Regardless of the location of the color changing species, a protection layer may be added to control diffusion of the specie triggering the color change (e.g., the color change activator), and/or to prevent undesirable (e.g., premature) deblocking (e.g., the protective layer can be a light blocking packaging that prevents outside light from contacting a photosensitive, blocked, color changing specie during the manufacturing and/or commercial distribution of the device (e.g., protects prior to usage)).

The composition of the protective layer is dependent upon the particular color change activator. For example, the protective layer can comprise a thermoplastic, e.g., a thermoplastic having an oxygen diffusion (e.g., an oxygen permeability) of less than or equal to about 1.35 barrers, or more specifically, less than or equal to about 1.1 barrers, or, even more specifically, less than or equal to about 0.9 barrers. This layer (which can be part of the article and/or the packaging enclosing the article), for example, can comprise a polyvinyl alcohol (PVA), polyolefin (e.g., cyclic polyolefin), polyester, polyamide, and the like, as well as combinations comprising at least one of the foregoing, e.g., to reduce oxygen diffusion. The protective layer can also be a film with an adhesive that attaches the protective layer to the article until it is removed and ready to be used.

The protective layer materials may be treated or formulated to further enhance the protection characteristic (e.g., further limit oxygen diffusion). Treatments may include plasma treatment, vacuum deposition of an inorganic barrier layer (such as a metal or metal oxide layer), and the like, as well as combinations comprising at least one of the foregoing. Formulation enhancements include, for example, the addition of oxygen scavengers and/or the use of nano-fillers (e.g., nano-clays, and the like) to decrease the oxygen diffusion. These enhancements can be, for example, dispersed in the protective layer, and/or added separately in the form of a bag such as the oxygen scavengers commercially available from Sorbent Systems.com (IMPAK), Los Angeles, Calif.).

For example, the protective layer can be a packaging layer that has a low oxygen permeability (e.g., a permeability of less than or equal to about 0.5 Barrers, or more specifically, less than or equal to about 0.1 Barrers), and provides a seal around the medical article. The protective layer can be a packaging layer that is sealed under reduced pressure (e.g., vacuum sealed, optionally after flushing the package with an inert gas such as nitrogen). For example, the article can be a medical article in a multi-layer package. The first layer can be a color change activator (e.g., an oxygen, ethylene oxide, and so forth) permeable package (e.g. gas can diffuse through the first layer of packaging for example through a Tyvek™ (Dupont) sleeve). A second layer can have low color change activator permeability (e.g., oxygen permeability) and can contain scavengers to eliminate residual color change activator in the package. The amount of scavenger can be proportionate to the volume of color change activator present in the sealed package. Optionally, the sealed article can then be activated, such as by sterilization by gamma radiation. The packaging layer can inhibit exposure of the color changing specie to the color change activator. For example, the packaging layer can inhibit the exposure such that, after removal of the packaging and exposure to the color change activator, the color changing specie is capable of a CIELAB $\Delta E^*$ of greater than or equal to 5, or, more specifically, greater than or equal to about 10, or even more specifically, greater than or equal to about 20. Additionally, the packaging layer can inhibit the exposure such that, while the medical article is packaged (e.g., from the time the medical article is enclosed in the packaging layer until it is removed therefrom), the color changing specie has a CIELAB $\Delta E^*$ of less than or equal to 4, or, more specifically, less than or equal to about 3, or even more specifically, less than or equal to about 2, and, even more specifically, an immeasurable change.

In addition, or alternative, to the protective layer, a kinetics controller can be employed. The kinetics controller can be mixed with the color change additive and/or disposed in operable communication with the color change additive (e.g., disposed such that the kinetics controller can affect the kinetics of the color change additive; such as disposed in a layer adjacent to a layer with the color change additive such that it can diffuse into the color change additive layer. Kinetics controllers including acid, base, salt (organic and/or inorganic), photoacid generator, photolatent base, reducing agent, blocking group precursor, and the like, as well as combinations comprising at least one of the foregoing kinetics controllers.

In a drug container, it may be desirable to buffer against the variability in initial color by adding background colorant(s), that give the desired appearance (for instance a true amber color to shield the inside of the container from potentially harmful wavelengths as specified by the United States Pharmacopeia (USP), i.e., 290 nm to 450 nm). These additional colorants comprise organic dyes and/or pigments approved for use in food contact or drug applications and/or that do not migrate outside of the polymer matrix by greater than 50 parts per billion by weight (ppb) outside the polymer matrix upon extraction test using a mixture of water/ethanol (1:1 vol/vol) or heptane at reflux for 48 hrs; and that exhibit sufficient heat stability to retain their color under manufacturing conditions.

A method of making a medical article can comprise disposing the color changing specie in at least a portion of the article. For example, the color changing article can be disposed in a handle, an indicator button (or portion), and/or elsewhere in the article. As with other embodiments, the color changing specie can be in a blocked or active form. In the active form, after the color changing specie is exposed to the color change activator, the color changing specie will begin to change color. (Note, this color change can be substantially instantaneous or after a desired period of time.) Alternatively, and/or in addition, the color changing specie can be disposed in packaging, e.g., around medication (a container), wrap around a medical article, and so forth. As a result, as above, when an active color change additive is exposed to the color change activator, it will begin to change color.

If the color changing specie is in the blocked form (i.e., the inactive form of the color changing specie), it will not begin changing color until it has been deblocked. Employing the color changing specie in the blocked form can control the color changing process until a desired time (e.g., after the article has been exposed to a non-sterile environment and have been re-sterilized. For example, the article can be opened and used, or merely opened, thereby requiring sterilization prior to use with another patient. The sterilization process can deblock the color changing specie, thereby activating it. Consequently, on subsequent exposure to the color change activator, the color changing specie will begin the process of changing color. Deblocking can occur, for example, with steam, heating, sterilization, during manufacturing, with exposure to light (e.g., UV radiation, and the like), as well as with combinations comprising at least one of the foregoing.

In use, a packaged medical article comprising a color changing specie can be removed from the packaging. Once the article has been removed from the packaging, it is considered "used" since it may no longer be sterile, or otherwise usable, even if the article was only removed from the packaging without any further use thereof. The "used" article can then be reprocessed to clean and/or sterilize the article for subsequent use. If the article comprises a blocked color changing specie, the reprocessing can deblock the color changing specie such that, upon subsequent exposure to a color change activator, the color changes.

If the color change activator was active when the article was removed from the packaging, the used article could be sent to a reprocessor who can receive the used medical article. The reprocessor can clean and sterilize the used medical article and then send/return the medical article, e.g., for a subsequent use. An active color changing specie could have a CIELAB ΔE* from the time the used article was received to the time the article was sent for subsequent use of greater than or equal to about 10.

EXAMPLES

Example 1

A 15% solid polymethyl methacrylate (PMMA), leuco methylene blue (LMB), 1-methoxy-2-propanol solution was made in a nitrogen atmosphere. (Note the LMB used in the examples was stored in an environment to minimize moisture and light exposure, unless otherwise specified.) Using this solution, the interior walls of glass vials were coated and then left upside-down to dry in a nitrogen atmosphere. After 12 hours of drying, absorbance of the interior walls was measured. The absorbance was again measured after 6 hours and 22 hours of exposure to air. FIG. 3 illustrates the spectral changes observed in the vials after exposure to air. After 22 hours, the vials turned from a slightly tinted color to an intense blue/green coloration corresponding to the formation of methylene blue, and allowing authentication and detection of vial tampering.

Example 2

Three LMB (Tipsoc, benzoyl LMB, and t-Boc LMB) dyes were explored for their ability to selectively oxidize to methylene blue when exposed to ultraviolet (UV) light. Polycarbonate disc substrates were spin coated with a 15 wt % PMMA solution in 1-methoxy-2-propanol (Dowanol™ PM) containing 1 wt % of the LMB dye and either 0 wt %, 1.5 wt %, or 3 wt % of Sn(II) 2-ethylhexanoate, or 0 wt % or 1 wt % of camphor sulfonic acid, wherein the weight percentages were based on a total weight of the solution. Half of the Tipsoc sample disks were then coated with a polyvinyl alcohol solution in water (a polyvinyl alcohol coating forms an oxygen barrier). Half of the samples were stored in a room temperature nitrogen ($N_2$) environment, while the other half was stored in a humid (60% to 80% relative humidity) at 55° C., $N_2$ environment (pre-heating). Half of each disk was masked and then the disk was subjected to 14 seconds of UV radiation via a Xenon lamp. The difference in absorbance between the two sides of the disk was measured for the duration of the experiment.

Both sides of the disk turned blue after Xenon lamp exposure of the samples with Tipsoc LMB suggesting that heat generated by the lamp or UV has led to the deblocking of the protected (i.e., blocked) leuco dye. Samples containing Tipsoc and Sn(II) 2-ethylhexanoate (a reducing agent) had a higher absorption at 660 nm (Abs 660) independent of UV exposure. This may be a result of other tin species being present and acting as oxidizing agents or deblocking catalysts. There was a larger Abs 660 shift in UV-treated samples after exposure to oxygen (consistent with more deblocking of UV treated samples) corresponding to a larger color change.

The samples that used benzoyl LMB as the leuco dye showed no effect due to the pre-heating at 55° C. and were stable (little or no shift in UV-vis spectrum) in air. Initially, samples with camphor sulfonic acid had a lower Abs360 (lower concentration of LMB formed). After the samples containing camphor sulfonic acid were irradiated with UV or heated there was a slightly higher Abs360 than those with no camphor sulfonic acid. There was very little change in Abs660 observed. However, samples with camphor sulfonic acid, that were heat treated and exposed to UV, had a greater Abs660 (higher concentration of methylene blue) and therefore a greater color change.

Prior to UV exposure, samples using t-Boc as the blocking group for the LMB dye were stable (little or no shift in UV-vis spectrum) to heat (55° C.). There was some deblocking (formation of LMB $\lambda_{max}$ 360) when stored at 55° C. in the presence of camphor sulfonic acid. When exposed to WV, the t-Boc LMB samples showed deblocking (Abs360 increased) with exposure to UV (and not heat). This indicates that there was either more deblocking in samples with no camphor sulfonic acid or LMB was converted to methylene blue prior to inspection. There was also a higher Abs660 upon LN exposure. The greatest change in Abs660 (indicative of the formation of methylene blue) was seen in samples containing camphor sulfonic acid and with pre-heat (storing samples at 55° C.), which was consistent with the larger color change observed in the sample.

From this experiment it was determined that t-Boc LMB produces the greatest contrast between half disks exposed and those samples not exposed to UV. Additional experiments were conducted to optimize the contrast between exposed and non-exposed sides. It was found that the greatest contrast was achieved by using a solution containing 2 wt % camphor sulfonic acid, 2 wt % Sn(II) 2-ethylhexanoate, PMMA, and a 14 sec flash time, followed by a post heat in a 55° C. humid $N_2$ environment (60% to 80% relative humidity).

This example illustrates the effect of additional components such as acids and reducing agents in addition to the color changing specie (leuco dye) and the differences of behavior between different blocking groups. The coating or resin system can be employed alone, or in combination with a handling process to improve the contrast or the rate of the color change.

Example 3

A 15 wt % solid polymethyl methacrylate (PMMA), leuco methylene blue (LMB), 1-methoxy-2-propanol solution was made in a nitrogen atmosphere. Using this solution, the interior wall of a three-layer vial (polycarbonate-oxygen barrier layer-polycarbonate) was coated and then left upside-down to dry in a nitrogen atmosphere. After 12 hours of drying, the vial was partially filled with water that had been extensively degassed, capped using a clamp seal with Teflon septum, and removed from nitrogen atmosphere. The absorbance of the interior walls was measured using a Hewlett Packard UV-vis spectrophotometer to be 0.08 at 655 nm when the vial was removed from nitrogen atmosphere and exposed to ambient conditions. The absorbance at 655 nm was again measured after exposure to air for 2 hours, 25 hours, 75 hours, and 168 hours. During this time (0 to 168 hours) the absorbance at 655 nm increased to 0.70. The relatively small increase in absorbance indicates that some oxygen permeated into the coating on the inside of the bottle, converting some of the dye to its oxidized (absorbing) form. However, most of the dye remained in its colorless form. At 168 hours the 5 milliliters (ml) of degassed water was removed through the septum of the vial using a syringe and replaced with tap water to simulate the vial being tampered. Within several minutes after the "tamper" occurred, the absorbance of the vial increased to 0.84, corresponding to the rapid formation of methylene blue, the colored (absorbing) form of the dye. The absorbance at 655 nm of the internal walls of the coated vial continued to increase to 1.05 forty-four hours after being tampered.

Example 4

A resin formulation comprising polycarbonate resin ($M_W$=17,700 amu), a phosphite heat stabilizer (Doverphos S-9228), and 0.1 parts per hundred (phr) color changing specie (t-Boc LMB), was compounded on a Sterling single screw extruder (Ø 44 mm). The following temperature settings were used (in ° C.): Feed/Z1/Z2/Z3/Die=250/260/270/270/270. Pellets, which had a blue/purplish appearance, were packaged off the line into Foodsaver bags (low oxygen permeability nylon bags) sealed under vacuum. The material was then molded into 5.08×7.62 centimeter (cm) chips (3.2 millimeters (mm) thickness) on a Boy 15S molding machine using the following temperature profile: Feed/Barrel/Nozzle (° C.)=260° C./280° C./280° C. The chips, which appeared slightly green/amber after molding, were packaged into individual sleeves and placed in a vacuum-sealed FoodSaver bag to protect them for light and/or oxygen exposure. Color and spectral data were collected on a MacBeth 7000A spectrophotometer in transmission mode.

Color data was reported in the CEELAB color space, using a 10 degree observer and a D65 illuminant light source. Chips were measured after molding and exposure to air at ambient temperature. (The chips were shielded from light by an aluminum pan while being exposed to air.) The color and spectral data were recorded as a function of air (i.e., $O_2$) exposure time on an average of 5 chips. The results are presented in FIG. 4 and clearly show that the chips were darkening (decrease in lightness L* value) as a function of time, thereby confirming the visual observations (see pictures in FIG. 4). Because the decrease in L* value appears to be linearly dependent on the square root of the exposure time, the mechanism seems to be driven (i.e., limited) by the diffusion of oxygen in the polycarbonate chips. Hence, the kinetics of the process can be accelerated, decelerated, and/or delayed, for example, by using a resin matrix with different oxygen properties or by adding a reducing agent. After only 8 hours, the L* value (which was originally relatively high (L* greater than about 87)) dropped by about 3 units, which is a clearly visible change. After about 1 day, the L* value decreased by about 10 units. After two weeks of exposure, the part became extremely dark (L* of about 14), e.g., to the point that it was very difficult to perceive any visual color change. At that point, it was almost impossible to see through at the 3.2 mm thickness gage.

High-performance liquid chromatography (HPLC) analysis of both the pellets and the molded chip were carried out to investigate if the t-Boc blocking group was able to block the leuco dye (LMB) during both extrusion and molding. It was found that although there was still some t-Boc LMB remaining after extrusion, all the t-Boc LMB had been deblocked after molding. (Not to be limited by theory, it is believed that the initial amber color of the parts was probably due to the thermal decomposition of methylene blue formed in the extruded pellets.) The initial amber may depend on the extrusion conditions, the purity of the t-Boc LMB, and the nature of additives present in the resin formulation that could stabilize the t-Boc LMB or favor deblocking depending on their nature. In a drug container, it may be desirable to buffer against the variability in initial color by adding background colorant(s), that give the desired appearance (for instance a true amber color to shield the inside of the container from potentially harmful wavelengths as specified by the United States Pharmacopeia (USP), i.e., 290 nm to 450 nm).

FIG. 5 illustrates the spectral changes in the chips at 3.2 mm thickness due to air (oxygen) exposure. After only 8 hours, percent light transmission (% T) dropped to less than or equal to about 50% at 650 nm as a result of the formation of methylene blue in the resin. After about a day, % T at 650 nm was less than 30%, i.e., less than half its initial value. In about 3 to 4 days, % T at 650 nm fell below 5%. After about 2 weeks, further spectral changes become minimal and very hard to detect. The part blocked more than about 97% of the light at about 420 nm to about 680 nm, consistent with fact that it was extremely difficult to see through the part.

Example 5

Two resin formulations comprising polycarbonate resin ($M_W$=17,700 amu), a phosphite heat stabilizer (Doverphos® S-9228, commercially available from Dover Chemical Corporation) and a color changing specie (benzoyl LMB) at a respective loading of 0.1 and 0.5 phr were compounded on a Sterling single screw extruder (Ø 44 mm). Note the benzoyl LMB was stored in an environment to minimize moisture and light exposure.

The following temperature settings were used for the extruder (in ° C.): Feed/Z1/Z2/Z3/Die=250/260/270/270/270. Pellets, which were almost colorless, were packaged off the line into Foodsaver bags sealed under vacuum. The material was then molded into 5.08×7.62 cm chips (3.2 mm thickness) on a Boy 15S molding machine using the following temperature profile: Feed/Barrel/Nozzle (° C.)=260° C./280° C./280° C. The chips appeared almost colorless after molding illustrating the better heat stability of the benzoyl blocking group as opposed to the t-Boc. The chips were packaged into individual sleeves and placed in a vacuum-sealed FoodSaver bag to protect them from light and/or oxygen exposure. Color and spectral data were collected on a MacBeth 7000A spectrophotometer in transmission mode. Color data are reported in the CIELAB color space, using a 10 degree observer and a D65 illuminant light source. Chips were measured after molding and then exposed to air at ambient temperature. The chips were shielded from light by an aluminum pan while being exposed to air. Some chips were stored. The changes in light transmission of the 3.2 mm chips were recorded as a function of air (i.e., $O_2$) exposure time on an average of 5 chips. The results are presented in FIG. 7 for a loading of 0.1 phr of benzoyl LMB. Similar results were observed for the chips molded from a resin containing about 0.5 phr benzoyl LMB (see FIG. 8). A more significant spectral change was observed with an increased loading of benzoyl LMB for a given air exposure time. Interestingly, a higher loading of benzoyl LMB did not seem to significantly affect the initial color since the molded chips still appeared colorless before being exposed to air.

The spectral curves clearly show that the chips were changing color as time evolved (which is consistent with visual observations: the chip went from colorless to dark blue-green over time) from the oxygen exposure. From the curve, it can be seen that there is no methylene blue (MB) initially present in the chip (no specific absorption at about 650 nm). Also, the relatively flat curve seems to indicate that there was little, if any, MB formed during the extrusion that degraded during molding. It is noted that the oxygen sensitivity observed for the benzoyl LMB was a rather surprising result since benzoyl is one of the most stable blocking groups. Not to be limited by theory, because of the theoretical stability of the benzoyl, one could have expected no color change at all after extrusion/molding in response to oxygen only (i.e., blocked leuco form totally intact).

Example 6

The chips molded from the t-Boc LMB formulation from Example 3 were exposed to UV light using a Xenon flash lamp. The spectral curve was measured in absorbance mode as a function of UV exposure time. FIG. 6 shows the evolution of the spectrum at various intervals (14, 28 and 58 seconds). The picture illustrates the rapid changes in appearance from a green/amber color to a very dark (almost black color) when exposed to UV light. The results are consistent with the observations made in the coating formulations of Example 2 where the color change was accelerated by UV exposure. This example, therefore, illustrates the fact that the articles made using the color changing systems (and/or resins) can have both air and light sensitivity to provide a better protection against multiple modes of counterfeiting, tampering, and/or re-use.

Example 7

In this example, the color chips molded from the resin formulation containing 0.1 phr of benzoyl LMB were measured using a MacBeth spectrophotometer. Color data were recorded (CIELAB color space, using a 10 degree observer and a D65 illuminant light source) after molding and then the chips were sealed under vacuum in a Foodsaver bag. Another measurement was taken about a week later and the chips were placed back in the bag and resealed under vacuum. A final measurement was then taken after about another 2 weeks (total of 3 weeks under vacuum). As a comparison, color chips were also left exposed to air (shielded from light) and exposed to both air and light (on a table near a window). Table 1 below shows the average color data for 3 chips.

TABLE 1

|  | After molding | Sealed 1 week | Sealed 3 weeks | 3 weeks in air | 3 weeks in air + light |
|---|---|---|---|---|---|
| CIELAB L* | 95.20 | 94.90 | 94.70 | 91.60 | 83.70 |
| CIELAB a* | −0.59 | −0.60 | −0.70 | −4.09 | −7.35 |
| CIELAB b* | 3.02 | 3.00 | 2.90 | 1.48 | −1.20 |
| CIELAB ΔE* | — | 0.34 | 0.55 | 5.29 | 14.01 |

Considering that the bags were sealed using a very crude technique (Foodsaver system and bags which have a simple nylon barrier layer), the ΔE* color differences observed when the chips are stored in the bags were very small (less than 0.6 units even after 3 weeks) thus illustrating the ability to retain the articles in their original color. These differences are especially small in comparison to the color shifts observed after air exposure (especially in the presence of light). This example illustrates the ability to limit the oxygen sensitivity (and thus retain the color changing specie in its reactive form) by using an outer barrier layer with oxygen barrier properties. With a more refined vacuum sealing technology using purging inert gas and multiple vacuum suction steps, it should be possible to preserve the parts in their active form over an extended period of time (e.g., months and possibly years). In this case, it will be necessary to use outer layers with lower oxygen permeability (improved oxygen barrier performance). Note that to further limit the oxygen sensitivity, resins with a lower oxygen permeability than standard polycarbonate may be used as a matrix for the leuco dye. Such resins include, but are not limited to, the polymers, copolymers and blends described in U.S. patent Application Publications No. 20040043254 A1, filed Sep. 4, 2002, and commonly assigned herewith.

Example 8

In this example, the color chips molded from the resin formulation containing 0.5 phr of benzoyl LMB were measured using a MacBeth spectrophotometer. Color data were recorded (CIELAB color space, using a 10 degree observer and a D65 illuminant light source) directly in the sealed package after molding and after exposure to ambient light for 4 days (sample left on a table next to window). The results are reported in the Table 2 below.

TABLE 2

|  | Initial (in bag) | After 4 days (in bag) |
|---|---|---|
| CIELAB L* | 87.90 | 86.60 |
| CIELAB a* | −2.18 | −3.13 |

TABLE 2-continued

|  | Initial (in bag) | After 4 days (in bag) |
|---|---|---|
| CIELAB b* | 8.19 | 7.78 |
| CIELAB ΔE* | — | 1.66 |

The results compiled in Table 2 indicate that the color change can be attained by exposure to light, without exposure to oxygen, for example. In other words, this ability to undergo a color change upon light exposure in a sealed package could be used, for example, to enable a built-in shelf life indicator in a container or medical device.

The use of the indicator can enable a medical professional to be able to check: (1) the number of times a device has been reprocessed by looking at the marking, (2) the life of the equipment (and/or medication) due to color change in an unopened article, and/or (3) whether an article has been tampered with and/or used, and the like. In addition, it would be also possible to a medical professional (or to re-processor or a third party) to "terminate" the life of a device by exposing it to a certain medium (e.g., light source, or the like) that would change its color in such a way that it comes clearly visible that the item has been "obsoleted" and cannot be re-used or reprocessed. These features are enabled by the color changing species that could be compounded in the resin to form a resin with built-in capability for light induced color change.

Example 9

Medical Devices With Built-in Usage Indicators Activated by Gamma Radiation Sterilization In this example, the color chips molded from the resin formulations containing 0.1 phr of benzoyl LMB were double sealed under vacuum using a Foodsaver system (and Foodsaver oxygen barrier bags) to protect them from oxygen exposure, then placed in a brown paper envelope and in a box. The packing density in the box was maintained to a level below 0.26 to comply with the gamma radiation sterilization guidelines. The box containing the chips was sent to IBA Sterigenics in Westerville, Ohio (USA) for gamma radiation sterilization using a Cobalt 60 irradiator system. The final exposure dose for the box was recorded (28.7 kiloGray (kGy), where 1 Gray is a unit measuring the irradiation energy which corresponds to 1 joule per kilogram (J/kg)). The chips were then unsealed and exposed to air (i.e., oxygen) in the absence of direct light exposure (using aluminum pans to shield the parts from light). Color data were recorded (CIELAB color space, using a 10 degree observer and a D65 illuminant light source) after unsealing the package and at various exposure times ranging from 1 to 20 days. The color shifts (CIELAB ΔE*) to the color measured right after unsealing the parts exposed to gamma radiation are reported in Table 4. The data for chips of the same composition that were not exposed to gamma radiation (i.e., not sterilized) are also reported in Table 4.

TABLE 3

|  | O₂ exposure (days): CIELAB ΔE* | | | |
|---|---|---|---|---|
|  | 1 | 2 | 3 | 20 |
| 0.5 phr BLMB (with GR) | 7.7 | 14 | 19.9 | 45.2 |
| 0.5 phr BLMB (no GR) | 1.7 | 3.3 | 5.0 | 19.9 |
| 0.1 phr BLMB (with GR) | 6.3 | 11.5 | 16.5 | 38.7 |
| 0.5 phr BLMB (no GR) | 0.7 | 1.24 | 1.8 | 6.9 |

Note that the color shifts observed correspond essentially to a negative shift in the b* value, which is consistent with the fact that the parts visually turn to a blue color. When looking at the changes in the spectral curve as a function of time, it appears that this shift in the b* value is essentially caused by the increase in absorption at about 650 nm which corresponds to the formation of methylene blue in the material. It must be noted that such color shifts greater than 10 units, and especially greater than 20 units can be immediately picked up by an untrained eye. It must be emphasized that the color differences observed for parts that have been exposed to gamma radiation are significantly larger (6 to 7 times larger) than those observed by only exposing the molded parts to oxygen in the absence light. This examples illustrates the fact that it is possible to create resins containing blocked leuco dyes that will get deblocked during gamma radiation sterilization and could be used as a built-in open package/usage indicator for medical devices when combined with an oxygen barrier (and/or oxygen scavenging) packaging material.

Some of the blocked leuco dyes described above that produce a blue/violet color in their oxidized form and can be incorporated into a polycarbonate resin, such as the benzoyl-leuco methylene blue, lose their blocking group during gamma radiation sterilization and become highly oxygen sensitive. If exposed to oxygen during and/or after sterilization, the oxidized (i.e., blue/violet color) form of the dye is obtained.

In one embodiment illustrated in the previous examples, this color changing specie can be used to build a usage or open package indicator. Another interesting use of this technology could be the active color compensation of gamma radiation sterilized resin. Gamma radiation sterilization can degrade polycarbonate resin and lead to an increase in the yellowness index (or YI) of the material as determined per ASTM E313 (D1925). Such increase can be associated with a visible change in the appearance of the material that can also be associated with the perception of defective products at the customer. By using blocked leuco coloring matter, it is possible to create resins for medical devices that will undergo no or even a negative YI shift when the material gets exposed to increasing doses of radiation (e.g., going from 25 kGy to 50 kGy to 75 kGy). This is due to the fact that the greater the radiation dose, the more leuco dye gets deblocked, and therefore the more blue/violet color gets formed in the presence of oxygen. This controlled color change induced by the formation of the oxidized form of a leuco dye upon gamma radiation sterilization may also be used in other applications to determine the dosage of gamma radiation exposure that a material (or device) has been exposed to.

Various methods of controlling the number of uses of an article, and detecting tampering have been developed. Many of these methods render the article unusable; e.g., a component and/or portion of the article melts, changes, degrades, or the like, such that the article no longer useable. The present technology enable the identification of tampering, use, re-sterilization (e.g., sterilization after a use), without affecting the structural integrity of the article (e.g., without affecting the mechanical functionality of the article). Optionally, the color changing specie can be designed to affect the functionality of the article (e.g., can be disposed in an area that should be transparent, such that the area be come opaque), or can be disposed so as not to affect functionality (e.g., the color of a handle on an instrument changes color). This process can also be used to simplify warranty expiration. If, for example, a warranty expires after a first use, the color changing specie can be disposed in the article such that it causes a color change that obscures information on the article (e.g., manufacturer information, warranty information, serial number, and the like).

This technology can be employed in pharmaceutical applications (e.g., medicine containers such as bottles, bubble wrap packages, and the like), medical articles (e.g., instruments (e.g., trocar, syringe, scalpel, tubing (e.g., suction tubing, intravenous tubing, and the like)), packaging around sterile items (such as bandages, gauze, instruments (scalpel, mirror, pick, drill, and the like))), and the like, as well as many other applications. Based upon the location of the color changing specie, and the state of the color changing specie (blocked or active), different activities can be identified.

This technology can be implemented in a variety of different ways. For example, some devices may have optional portions which may or may not be removable. The color changing specie could be localized in one of the optional portions. For example, if a manufacturer wished to make certain versions of a medical device wherein the device includes the color-changing technology, and also wished to make different versions of the device wherein the device did not include the technology, then this might be accomplished by designing a device containing an optional portion wherein the color change is observed with respect to the optional portion. The optional portion may or may not perform a function, which may or may not be necessary or useful in addition to its indicating function. Alternatively, certain versions of a medical device including the optional portion described above could include the optional portion with the color changing technology and other versions could include the optional portion wherein the optional portion does not have the color changing technology.

Various visual highlight techniques could be used to highlight the color changing technology. For example, the color change could render an asymmetric color scheme of a device symmetrical or vice versa. The color changing technology could be used in letter or other pattern-shaped configurations to make text, logos, trademarks, and/or other patterns (e.g., the universal biohazard symbol), substantially appear or disappear upon activation of the color change. Brightly colored plastic or special visual effects in the plastic (e.g., a metallic flake appearance) could be used to visually emphasize the portion of the device affected by color change. Different color combinations may be used to enhance contrast. Color change may be from at least substantially transparent to substantially opaque and vice versa. Alternatively, color change can be from one hue to another, or darker to lighter.

The color changing additive can be included in thermoplastic on the surface of the device. However, to better protect against possible ways to defeat the color changing technology it is often better to have an outer transparent or translucent film (e.g., of plastic) over the plastic that contains the color changing specie. The outer film can help protect against attempts to reverse the color change, e.g., by photo bleaching, chemical processing, and so forth. It is possible to add some dye or other agent to the outer film to absorb radiation at wavelengths prone to causing photo bleaching. It is also possible to vary the composition and/or properties of the outer film in order to adjust the timing and/or sufficient conditions required to cause the color change reaction. In another embodiment, the outer film could lose its integrity (e.g., dissolve) in response to certain stimulus (e.g., autoclaving), thereby affecting the behavior of the color change by affecting its exposure to a stimulus. In another embodiment a protective film could be manually removed (e.g., by the user) to hasten or initiate the color change and/or the film could be placed such that its removal is essential prior to effective use of the device.

The color changing technology can be combined with other authentication mechanisms including, without limitation, incorporating identifying data on the medical device (e.g., by laser writing or marking), or including certain forensic tagging molecules or endcapping molecules in the thermoplastic resins used to manufacture the device, or including certain dyes or dye combinations in the device (e.g., fluorescent, photochromic, etc.)

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A medical article, comprising:
   a plastic portion; and
   a blocked color changing specie;
   wherein the blocked color changing specie is capable of being active after post-processing, and wherein the post-processing is different than manufacturing processes employed to make the medical article; and
   wherein the active color changing specie is capable of changing color after exposure to a color change activator; and
   wherein the post-processing is selected from the group consisting of ethylene oxide sterilization, enzymatic cleaning, gamma radiation, disinfecting solution, and combinations comprising at least one of the foregoing post-processing.

2. The medical article of claim 1, wherein the blocked color changing specie comprises a blocked leuco dye having the formula:

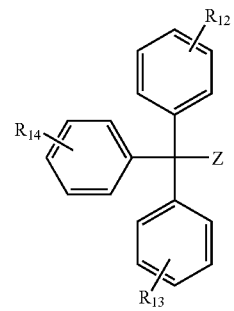

Formula III wherein Z is selected from the group consisting of O-acyl, O-aryl, O-alkyl, N-acyl, N-aryl, N-alkyl, O-silyl, S-alkyl, S-aryl, Si-alkyl, Si-aryl, Si-alkoxy, sulfonyl ($-O-SO_2-R_{15}$), a photolabile carbonyl group ($-CO-D$), an amide group, and a carbamate, and combinations comprising at least one of the foregoing Zs;
where $R_{15}$ comprises selected from the group consisting of an organic substituent;

wherein D comprises an aryl group;
wherein $R_{12}$-$R_{14}$ are, individually, selected from the group consisting of hydrogen, alkyl-amino groups, aryl-amino groups, halogens, alkoxy groups, aryloxy groups, acyl groups, aryl groups, alkyl groups, and combinations comprising at least one of the foregoing.

3. The medical article claim 1, wherein the blocked color changing specie comprises a blocked leuco dye having the formula:

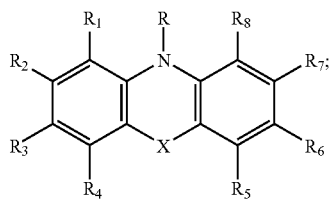

wherein X is O or S;

wherein $R_1$ to $R_8$ are, individually, selected from the group consisting of a halogen atom, a hydroxy group, an amino group, an alkyl group, an alkylamino group, a dialkylamino group, an alkyl ether group, a cycloalkyl group, a cyclic ether group, an aryl group, an aryl ether group, a heterocyclic group, a sulfonyl group, a carbonyl group, an ester group, and a carbonate group;
wherein R is the block and comprises a substituent that forms a bond with the leuco dye, wherein the bond is selected from the group consisting of urethane, amide, and a thioamide bonds, and wherein the substituent is selected from the group consisting of acyl groups ester groups and, thioester groups.

4. The medical article of claim 1, wherein the blocked color changing specie is photosensitive, and further comprising a light blocking packaging, wherein the light blocking packaging is capable of preventing exposure of the blocked color changing specie to light.

5. The medical article of claim 1, wherein the color change does not affect functionality of the medical article.

6. The medical article of claim 1, wherein the blocked color changing specie further comprises a blocking group selected from the group consisting of a carbamate, thiocarbamate, enamine, imine, acetal, sulfenyl, sulfonyl, phosphoryl, alkyl, imide, amide, benzylic moiety, peptide moiety, protein moiety, and combinations comprising at least one of the foregoing blocking groups.

7. The medical article of claim 1, wherein the plastic portion comprises a thermoplastic resin.

8. The medical article of claim 7, wherein the plastic portion comprises polycarbonate.

9. The medical article of claim 7, wherein the plastic portion comprises polymethyl methacrylate.

10. The medical article of claim 1, wherein the post processing comprises enzymatic cleaning.

11. The medical article of claim 1, wherein the post processing comprises using a disinfecting solution.

12. A medical article, comprising:
a plastic portion; and
a blocked color changing specie;
wherein the blocked color changing specie is capable of being active after post-processing, and wherein the post-processing is different than manufacturing processes employed to make the medical article; and
wherein the active color changing specie is capable of changing color after exposure to a color change activator; and
wherein the active color changing specie comprises a dye having a formula selected from the group consisting of Formula IV and Formula V:

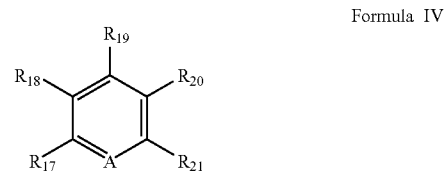

Formula IV

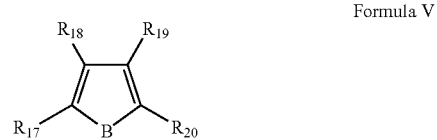

Formula V wherein A is selected from the group consisting of C—$R_{22}$, NH, O, S+, and N—$R_{21}$;
wherein B is selected from the group consisting of C—$R_{22}$, NH, O, S, and N—$R_{22}$; and
wherein $R_{17}$-$R_{22}$ are, individually, selected from the group consisting of H, alkyl, aryl, acyl, halogen, thiocarbamate, enamine, imine, acetal, sulfenyl, sulfonyl, phosphoryl, imide, and combinations comprising at least one of the foregoing.

13. The medical article of claim 12, wherein the blocked color changing specie comprises a blocking group selected from the group consisting of —CO-phenyl, —$SO_2$—$C_6H_5$, —CO—C—$(CH_3)_3$, —$CO_2C_2H_5$, —CO-phenyl-$NH_2$, —CO-phenyl-alkyl, —CO-phenyl-alkoxy, —CO-phenyl-halogen, —$SO_2C_4H_9$, -tosyl, and combinations comprising at least one of the foregoing blocking groups.

14. A medical article, comprising:
a plastic portion; and
a blocked color changing specie;
wherein the blocked color changing specie is capable of being active after sterilization;
wherein the active color changing specie is capable of changing color after exposure to a color change activator.

15. The medical article of claim 14, wherein the sterilization comprises gamma radiation sterilization.

16. The medical article of claim 14, wherein the sterilization comprises electron beam sterilization.

17. The medical article of claim 14, wherein the sterilization comprises ethylene oxide sterilization.

18. The medical article of claim 14, wherein the sterilization comprises autoclaving.

* * * * *